(12) United States Patent
Smoter

(10) Patent No.: US 6,174,866 B1
(45) Date of Patent: Jan. 16, 2001

(54) EDIBLE ANTI-PARASITE MEDICATION FOR DOMESTICATED ANIMALS

(76) Inventor: Rosemary Smoter, 2737 Wixom Rd., Milford, MI (US) 48381

(*) Notice: Under 35 U.S.C. 154(b), the term of this patent shall be extended for 0 days.

(21) Appl. No.: 09/421,601

(22) Filed: Oct. 20, 1999

Related U.S. Application Data

(60) Provisional application No. 60/104,898, filed on Oct. 20, 1998.

(51) Int. Cl.$^7$ ................................................ A61K 31/70
(52) U.S. Cl. .............................. 514/30; 424/408
(58) Field of Search ................. 514/30; 424/408

(56) References Cited

U.S. PATENT DOCUMENTS 5,346,698 * 9/1994 Abercrombie ................. 429/405
5,725,853 * 3/1998 Dennis et al. ................. 424/433

* cited by examiner

*Primary Examiner*—Elli Peselev
(74) *Attorney, Agent, or Firm*—Goldstein & Canino

(57) ABSTRACT

An antiparasitic medication for controlling and treating a wide variety of parasites in a herbivorous domesticated animal. The antiparasitic medication contains a mixture of ivermectin in a base of an alfalfa derivative. The antiparasitic medications are provided as pellets or fine granules or powders or other suitable feed application to avoid the use of injections in the animal, and to avoid stress and dangerous administration practices that could cause severe injury to both the care giver and the animal.

3 Claims, No Drawings

EDIBLE ANTI-PARASITE MEDICATION FOR DOMESTICATED ANIMALS

CROSS REFERENCES AND RELATED SUBJECT MATTER

This application relates to subject matter contained in provisional patent application Ser. No. 60/104,898, filed in the United States Patent Office on Oct. 20, 1998.

BACKGROUND OF THE INVENTION

The present invention relates to an antiparasitic medication for domesticated animals. In particular, the invention relates to an antiparasitic medication comprising ivermectin in an easily consumable carrier, for treating a vast variety of parasites.

Mankind has coexisted with domesticated animals for eons. Often, humans live with domesticated farm animals, such as camels, cows, horses, donkeys or the like, in their households or in close proximity thereto. These animals serve a variety of functions, including milk production and providing meat.

Unfortunately, equine or bovine animals are unable to defend themselves from parasitic infection. As a result, humans must bear the responsibility of preventing or treating parasitic infiltration of these animals.

Medicinal compounds have been disclosed that attempt to alleviate the problems of parasitic infections in animals. For example, U.S. Pat. No. 4,873,224 to Linn et al. discloses avermectin compounds that act as anti-parasitic agents. Avermectin compounds are series of macrolides, each of which is substituted thereon at the 13-position with a 4-($\alpha$-L-oleandrosyl)-$\alpha$-L-oleandrose group.

Ivermectin, a commercially available parasiticide sold under the trademarked name IVOMEC®, is well known for the treatment and control of internal and external parasites of cattle and swine.

Unfortunately, ivermectin is generally administered by injection, which frequently causes abscesses and requires a veterinarian to administer it. As a result, animals have a high traumatization rate and resist this application, sometimes violently and dangerously. There are "pour on" ivermectin compounds, which cause hair and fiber loss in the animals. Alternately, one may use an ivermectin paste, which also is disadvantageous in that it is inefficient and causes animals to resist treatment because of its taste. Consequently, there is a need for a new manner of administration so that the Ivermectin can be consumed by animals without resulting in any of the above-mentioned problems.

While the prior art compounds may be suitable for the particular purpose employed, or for general use, in terms of the combined formulations hereafter cited, they are inadequate for the purposes of the present invention as disclosed hereafter.

SUMMARY OF THE INVENTION

It is an object of the present invention to provide a antiparasitic medication for controlling and treating a wide variety of parasites in herbivorous farm animals. Accordingly, an antiparasitic medication is provided that contains an ivermectin derivative in an easily consumable carrier.

It is another object of the present invention to provide an antiparasitic medication that does not need to injected into animals. Accordingly, an antiparasitic medication is disclosed that may be provided as pellets or fine granules so that it may be easily consumed by animals.

It is a further object of the invention to provide an antiparisitic medication which is easily metabolized by the animal. Accordingly, the antiparisitic medication is embodied within an alfalfa pellet.

The invention is an antiparasitic medication for controlling and treating a wide variety of parasites in a herbivorous domesticated animal. The antiparasitic medication contains a mixture of ivermectin in a base of an alfalfa derivative. The antiparasitic medications are provided as pellets or fine granules or powders or other suitable feed application to avoid the use of injections in the animal, and to avoid stress and dangerous administration practices that could cause severe injury to both the care giver and the animal.

To the accomplishment of the above and related objects, the invention may be embodied in the form described in the accompanying description. Variations are contemplated as being contemplated as being part of the present invention, limited only by the scope of the claims.

DESCRIPTION OF THE INVENTION

The present invention relates to an antiparasitic medication for treating and controlling various types of parasites in herbivorous farm animals. As is well known, herbivorous farm animals live by grazing on grass or plants. Plants often get infected with parasites, which get conveyed to the grazing animals.

The present invention has particular utility in effectively destroying worms and parasites which are primarily responsible for adverse physiological effects in farm animals. To treat these parasitic infections, the present invention provides a mixture comprising an ivermectin compound derivative in an alfalfa base.

Ivermectin compounds, processes for their preparation, and their utility are disclosed and described in U.S. Pat. No. 4,963,667 to Chin et al., U.S. Pat. No. 4,333,925 to Buhs et al., U.S. Pat. No. 4,310,519 to Albers-Schonberg et al. and U.S. Pat. No. 4,199,569 to Chabala et al., which are incorporated by reference herein.

It is known that ivermectin compounds are metabolized to their corresponding esters which have been found as mixtures of various fatty acids in the fatty tissue of host animals. The fatty acid derivative compounds are a part of a fatty acid mixture found in the fatty tissue of host animals, which indicates that a host animal may not have to metabolize the resulting compounds, and the resulting compounds could be directly efficacious upon administration to the animals.

As a result, the derivative compounds of ivermectin are useful as anthelmintics and insecticides. The disease or group of diseases for which the ivermectin derivative compounds can be used as an antiparasitic agent are disclosed and particularly described in the above identified patent by Buhs et al.

Ivermectin derivative compounds are macrocyclic alcohols (i.e., cyclic compounds having rings containing seven or more carbon atoms) having straight chain or branched fatty acids of from about $C_2$ to about $C_{20}$. The process for making these ivermectin compounds and their structural features are disclosed and particularly described in the above identified patent by Chin et al.

It is possible to prepare the desired antiparasitic medication by mixing an adequate amount of the ivermectin derivative within a base substance. Alfalfa or Alfalfa derivative based compounds are preferred as the base substance.

Once a mixture of the desired composition has been achieved, capsules of desired size may be manufactured from the mixture. According to the preferred form, the antiparasitic medication is provided as pellets or fine granules that may be easily mixed in the food or drink of the animals for easy consumption. It is further preferred to mix these alfalfa based pellets with sweet feed before tendering said mix to the animals for consumption.

Many specific details contained in the above description merely illustrate some preferred embodiments and should not be construed as a limitation on the scope of the invention. Accordingly, many other variations are possible within the true spirit of the present invention.

What is claimed is:

1. A method of treating domesticated animals for parasites, comprising the steps of:

mixing ivermectin in an alfalfa base;

forming said mixture into pellet form;

feeding the animal the pellets.

2. The method of treating domesticated animals for parasites as recited in claim 1, wherein the step of feeding the animal is preceded by mixing the pellet with sweet feed.

3. A method of treating domesticated animals for parasites, comprising the step of:

feeding an animal an alfalfa pellet containing ivermectin.

\* \* \* \* \*